United States Patent
Le et al.

(10) Patent No.: US 9,204,966 B2
(45) Date of Patent: Dec. 8, 2015

(54) PENILE PROSTHESIS

(71) Applicant: Northwestern University, Evanston, IL (US)

(72) Inventors: Brian V. Le, Chicago, IL (US); David C. Dunand, Evanston, IL (US); Kevin T. McVary, Golf, IL (US); Alberto Colombo, Chicago, IL (US)

(73) Assignee: Northwestern University, Evanston, IL (US)

( * ) Notice: Subject to any disclaimer, the term of this patent is extended or adjusted under 35 U.S.C. 154(b) by 118 days.

(21) Appl. No.: 13/682,179

(22) Filed: Nov. 20, 2012

(65) Prior Publication Data

US 2013/0131443 A1    May 23, 2013

Related U.S. Application Data

(60) Provisional application No. 61/629,531, filed on Nov. 21, 2011.

(51) Int. Cl.
| | | |
|---|---|---|
| *A61F 2/26* | (2006.01) | |
| *A61L 31/14* | (2006.01) | |
| *A61L 27/06* | (2006.01) | |
| *A61L 27/50* | (2006.01) | |

(52) U.S. Cl.
CPC . *A61F 2/26* (2013.01); *A61L 27/06* (2013.01); *A61L 27/50* (2013.01); *A61L 31/14* (2013.01); *A61F 2210/0023* (2013.01); *A61L 2400/16* (2013.01)

(58) Field of Classification Search
CPC .......... A61M 29/02; A61F 2/885; A61F 2/88; A61F 2/90; A61F 2/91; A61F 2/915; A61F 2/92
USPC .............. 600/38–41; 623/1.14, 1.15; 606/195
See application file for complete search history.

(56) References Cited

U.S. PATENT DOCUMENTS

| | | | | |
|---|---|---|---|---|
| 5,354,309 | A * | 10/1994 | Schnepp-Pesch et al. | 606/198 |
| 5,456,694 | A * | 10/1995 | Marin et al. | 623/1.11 |
| 6,273,908 | B1* | 8/2001 | Ndondo-Lay | 623/1.43 |
| 7,794,494 | B2* | 9/2010 | Sahatjian et al. | 623/1.42 |
| 7,815,674 | B1* | 10/2010 | Ragazzo | 623/1.23 |
| 8,092,514 | B1* | 1/2012 | Khosravi et al. | 623/1.15 |
| 2005/0125053 | A1* | 6/2005 | Yachia et al. | 623/1.15 |
| 2005/0228482 | A1* | 10/2005 | Herzog et al. | 623/1.15 |

OTHER PUBLICATIONS

J. Patrick Selph et al. Penile prosthesis infection: approaches to prevention and treatment, Urol. Clin. N. Am. 38:227-235 (2011).
R. Vaidyanathan, "Shape-Memory Alloys," Kirk-Othmer Encyclopedia of Chemical Technology, pp. 1-13 (downloaded Nov. 7, 2011).
Daniel Udelson, "Biomechanics of male erectile function," J. R. Soc. Interface 4:1031-1047 (2007).

* cited by examiner

*Primary Examiner* — Samuel Gilbert
(74) *Attorney, Agent, or Firm* — Klintworth & Rozenblat IP LLC

(57) ABSTRACT

A penile prosthesis is disclosed that can alternate between an erect and flaccid state based on the shape memory properties of an exoskeleton that is responsive to increases and decreases in temperature. The exoskeleton consists of a shape memory alloy, such as nitinol, which in the erect configuration can radially expand and resist axial loads and buckling forces during coitus. The shape memory alloy is temperature-tuned to undergo a change to an erect state under external application of heat and can revert to a flaccid state with cooling below resting penile temperature.

27 Claims, 15 Drawing Sheets

Austenite

Austenite

Austenite

Martensite

PENILE PROSTHESIS

CROSS-REFERENCE TO RELATED APPLICATIONS

This application claims benefit of priority under 35 U.S.C. 119 to U.S. provisional patent application Ser. No. 61/629,531, filed Nov. 21, 2011, and entitled "Penile Prosthesis," the contents of which are herein incorporated by reference in its entirety.

FIELD OF THE INVENTION

This invention relates generally to penile prostheses in the treatment of erectile dysfunction and more specifically to the radial expansion and changes in configuration from flaccid to erect state to simulate an erection. The proper functioning of the device relies on the ability of the prosthesis when implanted in the corpus cavernosum to expand cross-sectionally and straighten to the erect position during sexual intercourse.

BACKGROUND

Erectile dysfunction (ED) is a multifactorial disease that affects approximately 30 million American men and is continuing to increase along with the upsurge in diabetes, hypertension and cardiovascular disease. When first line and second line medications such as the phosphodiesterase 5 inhibitor class of medications or direct injections fail, surgical implantation of penile prostheses offers a permanent solution. Surgical implantation of prostheses is a known practical means of treating erectile dysfunction.

Two broad classes of penile prostheses are known in the prior art, the inflatable prosthesis and the semi-rigid prosthesis. The inflatable penile prosthesis aims to closely parallel a natural erection by shifting fluid from one area of the device, usually a reservoir, to the cylinders within the corpora cavernosa under hydraulic pressure to mimic the erect state. It relies on a closed system of reservoirs, pumps, valves and hydraulic pressure to produce a simulated erection sufficient for coitus. Consequently, the surgical implantation of this device is more complex is more prone to mechanical failure. Indeed only 67 to 88% are fully functional at 10 years, (Selph et al. *Penile prosthesis infection: approaches to prevention and treatment*, Urol. Clin. N. Am. 2011; 38(2): 227-235). The advantages of the inflatable prosthesis are that it appears more physiologic and does not exert constant pressure on surrounding tissues when in the flaccid state reducing the risk of erosion.

In contrast, the semi-rigid strikes a balance between being rigid enough for penetration, but malleable enough to allow positioning downwards when not in use. The advantages are that the device is simple, reliable, involves a smaller dissection, has fewer parts, and requires minimal dexterity to use. The disadvantages are that it appears constantly erect. It exerts more force on the surrounding tissues and has increased risk for erosion.

Thus there is a need for a surgical solution for men with refractory erectile dysfunction that appears as physiologic as possible, yet remains discrete. The penile prosthesis we propose meets the criteria for a discrete, physiologic-appearing, penile implant that can be used to treat ED. It has the advantages of the malleable prosthesis in that it only requires implantable cylinders and has no scrotal pump or abdominal reservoir, but then also has the advantages of an inflatable penile prosthesis in that with application of heat can produce a simulated erection with expansion of the cylinders. It is different from existing thermal-based solutions in that this device takes advantage of the fine-tuned properties of commercially available nickel-titanium alloys, notably their hysteresis and reliable shape-memory properties, as opposed to phase changes.

SUMMARY

In one aspect of the invention, a penile prosthesis that is implantable in the corpus cavernosum is disclosed wherein the prosthesis has a cylindrical outer contour along its longitudinal axis, is comprised of a shape memory alloy, and has a dimension that enlarges in response to an increase in temperature around said prosthesis.

In a second aspect of the invention, a penile prosthesis that is implantable in the corpus cavernosum is disclosed wherein the penile prosthesis is comprised of a single portion of a shape memory alloy having a cylindrical shape. The prosthesis comprises a backbone running along a longitudinal axis of the device and has loops circumferentially extending from the backbone. The device widens radially while maintaining a substantially cylindrical shape at or above a transition temperature.

In this aspect of the invention, the shape memory material comprising the apparatus is a nickel-titanium alloy. Doping with copper or chromium to adjust its response to temperature can further modify the nickel-titanium alloy.

In a third aspect of the invention, a penile prosthesis that is implantable in the corpus cavernosum is disclosed wherein the penile prosthesis is comprised of a single portion of shape memory alloy having a cylindrical shape. The prosthesis comprises a backbone running along a longitudinal axis of the device and has ribs circumferentially extending from the backbone. The device widens radially while maintaining a substantially cylindrical shape at or above a transition temperature.

In this aspect of the invention, the shape memory material comprising the apparatus is a nickel-titanium alloy. Doping with copper or chromium to adjust its response to temperature can further modify the nickel-titanium alloy.

In a fourth aspect of the invention, a penile prosthesis that is implantable in the corpus cavernosum is disclosed wherein the penile prosthesis is comprised of a single portion of shape memory alloy having a cylindrical shape. The prosthesis comprises a backbone running along a longitudinal axis of the device and has ribs circumferentially extending from the backbone. The backbone is comprised of a plurality of holes of a plurality of sizes and a plurality of shapes to provide a wider range of flexibility. The device widens radially while maintaining a substantially cylindrical shape at or above a transition temperature.

In this aspect of the invention, the shape memory material comprising the apparatus is a nickel-titanium alloy. The nickel-titanium alloy can be further modified by doping with copper or chromium to adjust its response to temperature.

In a fifth aspect of the invention, a penile prosthesis that is implantable in the corpus cavernosum is disclosed wherein the penile prosthesis is comprised of a single portion of shape memory alloy having a cylindrical shape. The prosthesis comprises a backbone running along a longitudinal axis of the device and has ribs circumferentially extending from the backbone. The device widens radially while maintaining a substantially cylindrical shape at or above a transition temperature.

In this aspect of the invention, the shape memory material comprising the apparatus is a nickel-titanium alloy. The nickel-titanium alloy can be further modified by doping with copper or chromium to adjust its response to temperature.

In a fifth aspect of the invention, a penile prosthesis that is implantable in the corpus cavernosum is disclosed wherein the prosthesis is comprised of a longitudinal axis, a backbone, and a plurality of loops. The backbone is comprised of a shape memory alloy and exhibits a left side and right side. The backbone is capable of maintaining a non-linear shape with respect to the longitudinal axis below a transition temperature, and is capable of substantially reverting to a linear shape defined by the longitudinal axis at or above a transition temperature.

The plurality of loops in this aspect of the invention may are comprised of a shape memory alloy. The loops are attached to both the left side and right side of the backbone and have an arcuate shape that defines a cylindrical contour of the apparatus. The loops widen radially while maintaining a substantially cylindrical contour at or above a transition temperature.

In this aspect of the invention, the shape memory material comprising the backbone and the plurality of loops is a nickel-titanium alloy. The nickel-titanium alloy can be further modified by doping with copper or chromium to adjust its response to temperature.

In an alternative of the fifth aspect of the invention, the plurality of loops having an arcuate shape are comprised of a first section and a second section. Both of these sections are able to define a cylindrical contour of the apparatus. When the apparatus is exposed to a temperature at or above the transition temperature, the first section widens radially while maintaining a substantially cylindrical contour and the second section radially contracts while maintaining a substantially cylindrical contour.

In a sixth aspect of the invention, a penile prosthesis that is implantable in the corpus cavernosum is disclosed wherein the prosthesis is comprised of a longitudinal axis, a backbone, and a plurality of ribs. The backbone is comprised of a shape memory alloy and exhibits a left side and right side. The backbone is capable of maintaining a non-linear shape with respect to the longitudinal axis below a transition temperature, and is capable of substantially reverting to a linear shape defined by the longitudinal axis at or above a transition temperature.

The plurality of ribs in this aspect of the invention is comprised of a shape memory alloy. The ribs are attached to both the left side and right side of the backbone and have an arcuate shape that defines a cylindrical contour of the apparatus. The ribs widen radially while maintaining a substantially cylindrical contour at or above a transition temperature.

In this aspect of the invention, the shape memory material comprising the backbone and the plurality of ribs is a nickel-titanium alloy. The nickel-titanium alloy can be further modified by doping with copper or chromium to adjust its response to temperature.

In an alternative of the sixth aspect of the invention, the plurality of ribs having an arcuate shape is comprised of a first section and a second section. Both of these sections define a cylindrical contour of the apparatus. When the apparatus is exposed to a temperature at or above the transition temperature, the first section widens radially while maintaining a substantially cylindrical contour and the second section radially contracts while maintaining a substantially cylindrical contour.

In a seventh aspect of the invention, a penile prosthesis that is implantable in the corpus cavernosum is disclosed wherein the prosthesis is comprised of a longitudinal axis, a backbone, and a plurality of ribs. The backbone is comprised of a shape memory alloy and exhibits a left side and right side. The backbone is capable of maintaining a non-linear shape with respect to the longitudinal axis below a transition temperature, and is capable of substantially reverting to a linear shape defined by the longitudinal at or above a transition temperature.

The plurality of ribs in this aspect of the invention is comprised of a shape memory alloy. The ribs are attached to both the left side and right side of the backbone and have an arcuate shape that defines a cylindrical contour of the apparatus. The ribs widen radially while maintaining a substantially cylindrical contour at or above a transition temperature.

In this aspect of the invention, the shape memory material comprising the backbone and the plurality of ribs is a nickel-titanium alloy. The nickel-titanium alloy can be further modified by doping with copper or chromium to adjust its response to temperature.

In an alternative of the seventh aspect of the invention, the plurality of ribs having an arcuate shape is comprised of a first section and a second section. Both of these sections define a cylindrical contour of the apparatus. When the apparatus is exposed to a temperature at or above the transition temperature, the first section widens radially while maintaining a substantially cylindrical contour and the second section radially contracts while maintaining a substantially cylindrical contour.

In an eighth aspect of the invention, a method of simulating an erection of a penis is disclosed wherein an implanted penile prosthesis comprising a shape memory alloy is heated to a temperature at which a dimension of the prosthesis enlarges.

DETAILED DESCRIPTION

Figure 1:
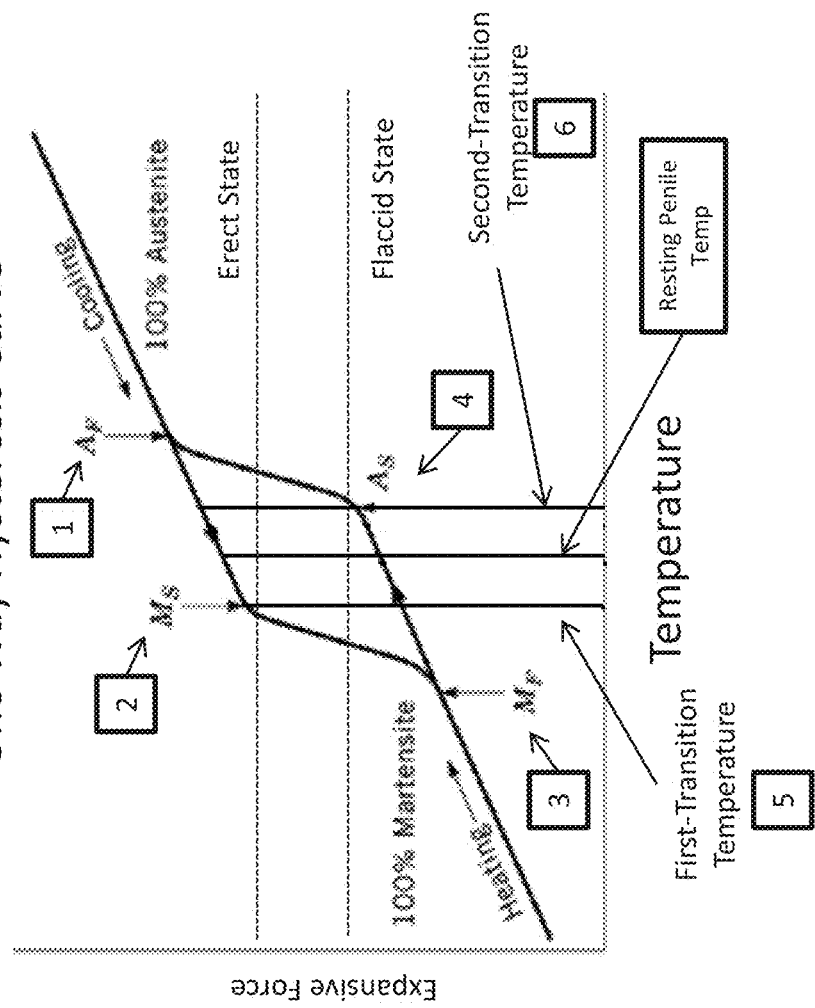
FIG. 1 is an example of a shape memory alloy hysteresis curve.

Prostheses for simulating a penile erection are disclosed herein. The prostheses disclosed herein may comprise a shape memory alloy. As is generally understood in the engineering arts, a shape memory alloy may be able to exhibit a shape recovery effect. The shape recovery aspect of a shape memory alloy is associated with the martensitic transformation. When an alloy of steel is heated to an austenite phase and then rapidly cooled to a martensitic metallic phase, the metallic martensitic phase remains upon heating over a small temperature range. In comparison, the martensitic transformation in a shape memory alloy is thermoelastic over a small temperature range. This means the martensitic metallic phase is transformed to the parent austenite metallic phase over a small increase in temperature, and then may be regained over a small decrease in temperature, (Shape-Memory Alloys, Kirk-Othmer Encyclopedia of Chemical Technology, downloaded Nov. 7, 2011).

The intermetallic phase in these alloys undergoes a displaced, shear-like transformation when cooled below a critical temperature designated as $M_S$ (martensitic start). Upon further cooling, to a temperature designated as $M_F$ (martensitic finish), the transformation is complete and the alloy is said to be in a martensitic state. When this martensitic is deformed, it undergoes a strain that is recovered when the alloy is heated. This recovery process starts at another critical temperature designated as $A_S$ (austenite start) and is completed at a higher temperature $A_F$ (austenite finish), (Shape-Memory Alloys, Kirk-Othmer Encyclopedia of Chemical Technology, downloaded Nov. 7, 2011).

There is a hysteresis associated with the formation of the martensitic metallic phase and its reverse transformation to the parent austenite metallic phase in a shape memory alloy. The temperatures $M_S$, $M_F$, $A_S$, and $A_F$ may depend on the particular base alloy. In a preferred embodiment of an invention disclosed herein, the base alloy may be a copper-aluminum-nickel alloy. The copper-aluminum-nickel alloy disclosed herein may be between about 28.00 atomic percent aluminum and 29.00 atomic percent aluminum, about 3.00 atomic percent nickel and about 4.00 atomic percent nickel, the balance copper. In a more preferred embodiment of an invention disclosed herein, the base alloy may be a nickel-titanium alloy. The nickel-titanium alloy disclosed herein may be between about 49.00 atomic percent nickel and about 51.00 atomic percent nickel, the balance titanium.

The temperatures $M_S$, $M_F$, $A_S$, and $A_F$ may also depend on the addition of an additive to the base alloy. In a preferred embodiment of the invention disclosed herein, the additive may be chromium. In this preferred embodiment, the amount of chromium may be between about 0.00 atomic percent and about 10.00 atomic percent of the base alloy's composition. In an alternative preferred embodiment of an invention disclosed herein, the additive may be copper. In this alternative preferred embodiment of an invention disclosed herein, the amount of copper may be between about 0.00 atomic percent and about 5.00 atomic percent of the base alloy's composition. In a further alternative preferred embodiment of an invention disclosed herein, the additive may be both chromium and copper. In this further alternative preferred embodiment, the amount of chromium may vary between about 0.00 atomic percent and about 10.00 atomic percent of the base alloy's composition, and the copper may vary between about 0.00 atomic percent and about 5.00 atomic percent of the base alloy's composition.

Shape memory alloys may exhibit two types of shape memory effects. The first, known as the shape memory effect, refers to the phenomenon wherein a shape memory alloy exposed to a mechanical deformation "remembers" and returns to pre-set shape upon exposure to heat. To repeat this event, the shape memory alloy must be cooled and mechanically deformed before it can return to its pre-set shape. In comparison, in a two-way shape memory effect the material can cycle between two pre-set shapes upon heating or cooling without mechanical deformation. For purposes of this disclosure, alloys exhibiting the shape memory effect are known as "shape memory alloys," and alloys exhibiting the two-way shape memory effect are known as "two-way shape memory alloys."

In a preferred embodiment a prosthesis disclosed herein may comprise a shape memory alloy. Referring to FIG. 1, in a preferred embodiment a prosthesis disclosed herein may exhibit a hysteresis curve comprising $A_F$ 1, $M_S$ 2, $M_F$ 3, and $A_S$ 4. As demonstrated in FIG. 1, $A_F$ is set above resting penile temperature. In this state, the prosthesis is substantially, if not completely, in its pre-set non-mechanically deformed shape. In this state, the implanted penile prosthesis may be able to impart expansive forces to the penile corpus cavernosa and tunica albuginea, and the penis may exhibit the increased radial and longitudinal growth experienced by an erect penis. In this state, the penis may appear erect.

Still referring to FIG. 1, an implanted prosthesis may then be exposed to a first-transition temperature 5 that coincides with $M_S$ 2. As demonstrated in FIG. 1, the first-transition temperature may be set below penile resting temperature. In a preferred embodiment, the first-transition temperature is between about 20 degrees Celsius and about 32 degrees Celsius. In this state, the amount of the alloy in the austenite phase begins to decrease and the amount of the alloy in the martensitic phase begins to increase. As the amount of the alloy in the martensitic phase begins to increase, the prosthesis may be able to begin losing its pre-set shape. As the temperature continues to decrease, the amount of the alloy in the martensitic phase increases until the prosthesis is substantially, if not completely, comprised of a martensitic phase. This point is denoted at $M_F$ 3. In this state, the prosthesis may be mechanically deformed. Since the prosthesis is implanted in the penile corpus cavernosa, the innate compressive forces of the penile corpus cavernosa may lead to mechanical deformation of the prosthesis. Alternatively, compressive forces from the tunica albuginea may lead to mechanical deformation. Additionally, deformation may be imparted through manipulation by the hands. In this state, the implanted prostheses impart less expansive forces to the penile corpus cavernosa and tunica albuginea than compared to the austenite phase and the penis may not exhibit the increased radial and longitudinal growth exhibited by an erect penis. Instead, the penis may appear flaccid and may be able to be discretely tucked away.

Still referring to FIG. 1, a penile prosthesis may then be exposed to a second-transition temperature 6 that coincides with $A_S$ 4. As demonstrated in FIG. 1, the second-transition temperature may be set above resting penile temperature. In a preferred embodiment, the second-transition temperature is between about 35 degrees Celsius and about 45 degrees Celsius. In this state, the amount of the alloy in the austenite phase begins to increase and the amount of the alloy in the martensitic phase begins to decrease. As the amount of the alloy in the austenite phase increases, the prosthesis begins to remember its pre-set shape. As the temperature continues to increase, the amount of the alloy in the austenite phases continues to increase until the prosthesis is substantially, if not completely, comprised of an austenite phase. This state is denoted in FIG. 1 as $A_F$ 1. The prosthesis in this state is substantially, if not completely, in its pre-set non-mechanically deformed shape. In this state, the implanted penile prosthesis may be able to impart expansive forces to the penile corpus cavernosa and tunica albuginea, and the penis may exhibit the increased radial and longitudinal growth experienced by an erect penis. In this state, the penis may appear erect.

Figure 2:
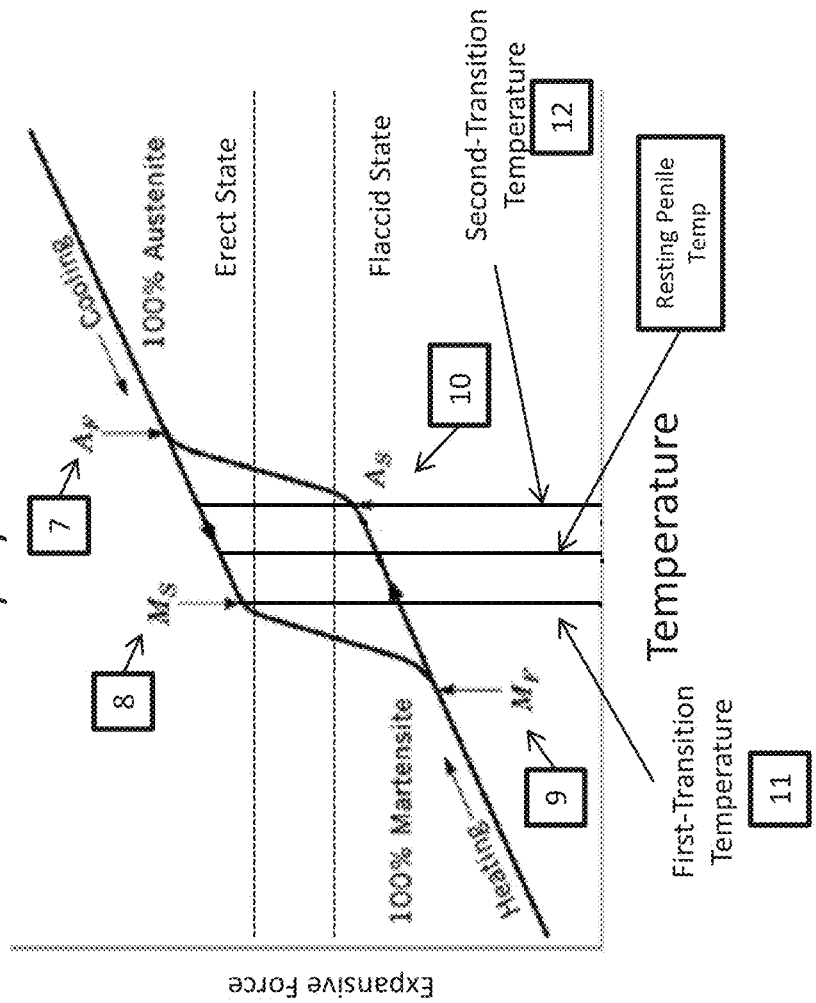
FIG. 2 is an example of a two-way shape memory alloy hysteresis curve.

In an alternative embodiment, the prostheses disclosed herein may comprise a two-way shape memory alloy. Referring to FIG. 2, in the alternative embodiment the prostheses disclosed herein may exhibit a two-way hysteresis curve. Referring to FIG. 2, in this alternative embodiment the prosthesis disclosed herein may exhibit a two-way hysteresis curve comprising $A_F$ 7, $M_S$ 8, $M_F$ 9, and $A_S$ 10. As demonstrated in FIG. 2, $A_F$ is set above resting penile temperature. In this state, the prosthesis may comprise a first pre-set shape. In this state, the implanted penile prosthesis may be able to impart expansive forces to the penile corpus cavernosa and tunica albuginea, and the penis may exhibit the increased radial and longitudinal growth experienced by an erect penis. In this state, the penis may appear erect.

Still referring to FIG. 2, an implanted prosthesis may then be exposed to a first-transition temperature 11 that coincides with $M_S$ 8. As demonstrated in FIG. 1, the first-transition temperature may be set below penile resting temperature. In a preferred embodiment, the first-transition temperature is between about 20 degrees Celsius and about 32 degrees Celsius. In this state, the amount of the alloy in the austenite phase begins to decrease and the amount of the alloy in the martensitic phase begins to increase. As the amount of the alloy in the martensitic phase begins to increase, the prosthesis may be able to begin losing its first pre-set shape and begins to remember a second pre-set shape. As the temperature continues to decrease, the amount of the alloy in the martensitic phase increases until the prosthesis is substantially, if not completely, comprised of a martensitic phase. This point is denoted at $M_F$ 9. In this state, the prosthesis is in its second pre-set shape. In this state, the implanted prostheses impart less expansive forces to the penile corpus cavernosa and tunica albuginea than compared to the austenite phase and the penis may not exhibit the increased radial and longitudinal growth exhibited by an erect penis.

Still referring to FIG. 2, a penile prosthesis may then be exposed to a second-transition temperature 12 that coincides with $A_S$ 10. As demonstrated in FIG. 2, the second-transition temperature may be set above resting penile temperature. In a preferred embodiment, the second-transition temperature is between about 35 degrees Celsius and about 45 degrees Celsius. In this state, the amount of the alloy in the austenite phase begins to increase and the amount of the alloy in the martensitic phase begins to decrease. As the amount of the alloy in the austenite phase increases, the prosthesis begins to remember its first pre-set shape. As the temperature continues to increase, the amount of the alloy in the austenite phases continues to increase until the prosthesis is substantially, if not completely, comprised of an austenite phase. This state is denoted as in FIG. 2 as $A_F$ 7. The prosthesis in this state is substantially, if not completely, in its first pre-set shape. In this state, the implanted penile prosthesis may be able to impart expansive forces to the penile corpus cavernosa and tunica albuginea, and the penis may exhibit the increased radial and longitudinal growth experienced by an erect penis. In this state, the penis may appear erect.

Figure 15:
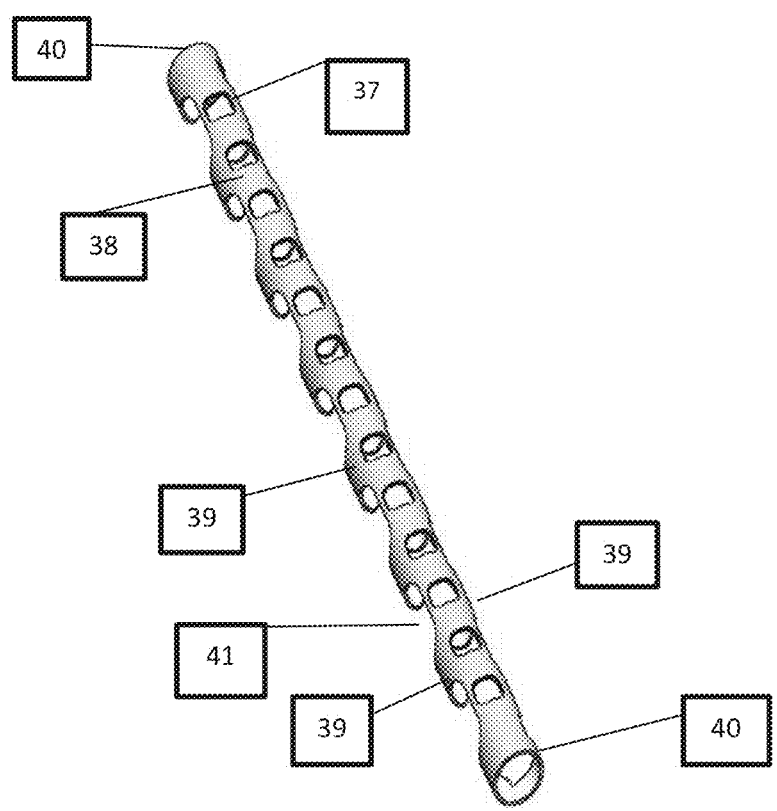
FIG. 15 is an example of a penile prosthesis comprising a backbone with a plurality of holes of a plurality of sizes and shapes made of one way memory alloy, also having ribs wherein the shape memory alloys are in a martensitic phase.

Referring to FIGS. 3 through 8, a penile prosthesis disclosed herein may be comprised of a single sheet 13 of a shape memory alloy. The penile prosthesis comprised of a single sheet 13 of memory alloy can be made through various methods. Memory alloy can be cut to a preferred embodiment by methods using but not limited to a laser, a water jet, or a cast molding. In a preferred embodiment the prosthesis may have a substantially cylindrical shape. The sheet may have a longitudinal axis 14 running through the length of the prosthesis, and a backbone 15 running with the longitudinal axis. While the transition temperature between flaccid/martensitic state and rigid/austenitic state is mostly dictated by the memory alloy properties, the level of flexibility and rigidity is regulated by the geometry of the prosthesis. Referring to FIG. 15, adding or removing memory alloy from the backbone can change the flexibility of the penile prosthesis. More specifically, flexibility can be changed by creating holes 37 in the prosthesis backbone. Holes 37 could comprise various sizes in surface area as long as not to exceed the surface area of the backbone 15 memory alloy. Holes 37 could also comprise various shapes including; squares, circles, ovals, rectangles, and diamonds. Additionally the backbone 15 widths may be altered to increase or decrease flexibility. The backbone 15 width should be equal to or less than one half the circumference of the cylindrical outer contour 40. The device may comprise at least two ribs 16 circumferentially extending from the backbone in a direction opposite to a circumferential extension of at least one adjacent rib.

Figure 3:
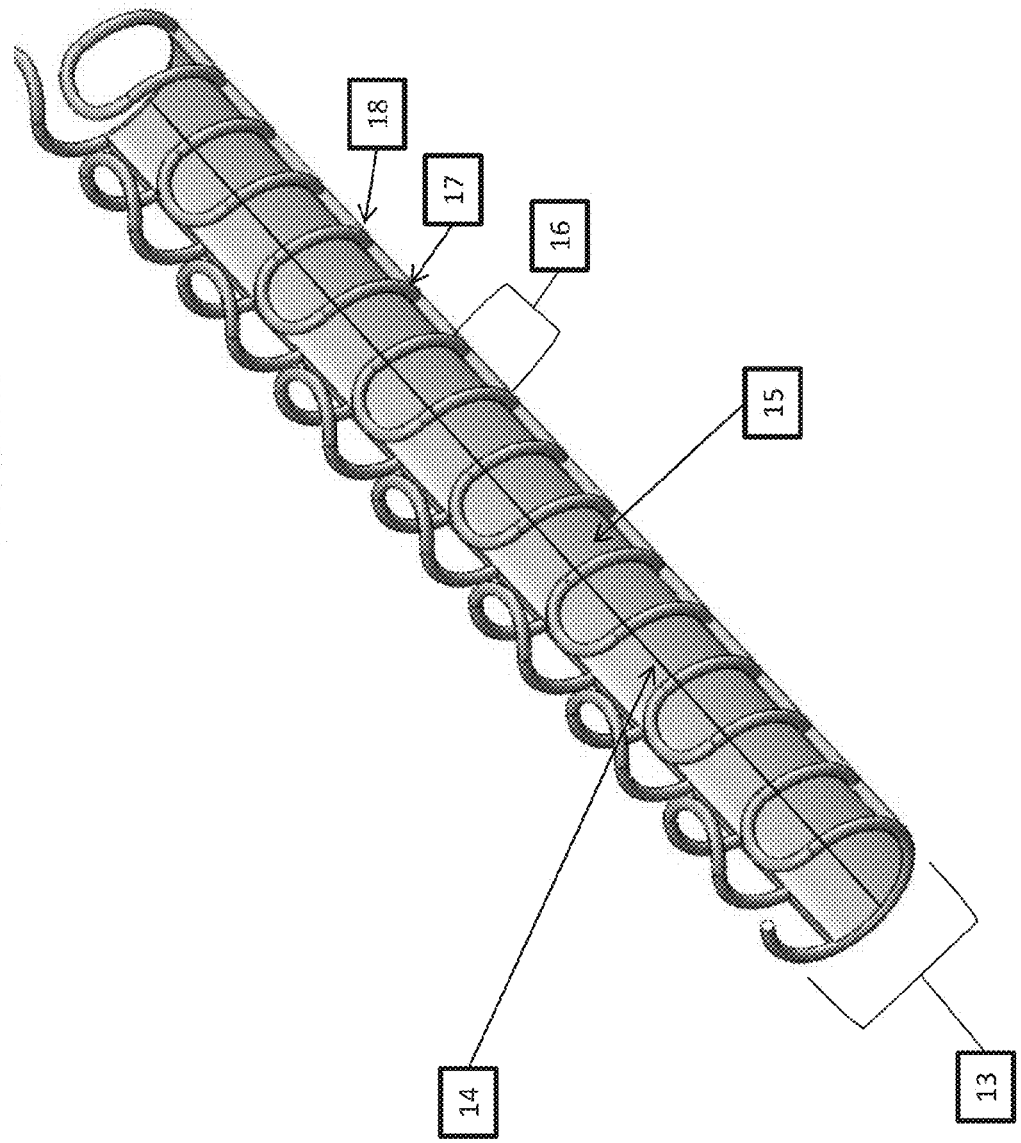
FIG. 3 is an example of a penile prosthesis comprised of a single portion of a shape memory alloy, has ribs in the shape of loops, and wherein the shape memory alloy is in an austenite phase.
Figure 4:
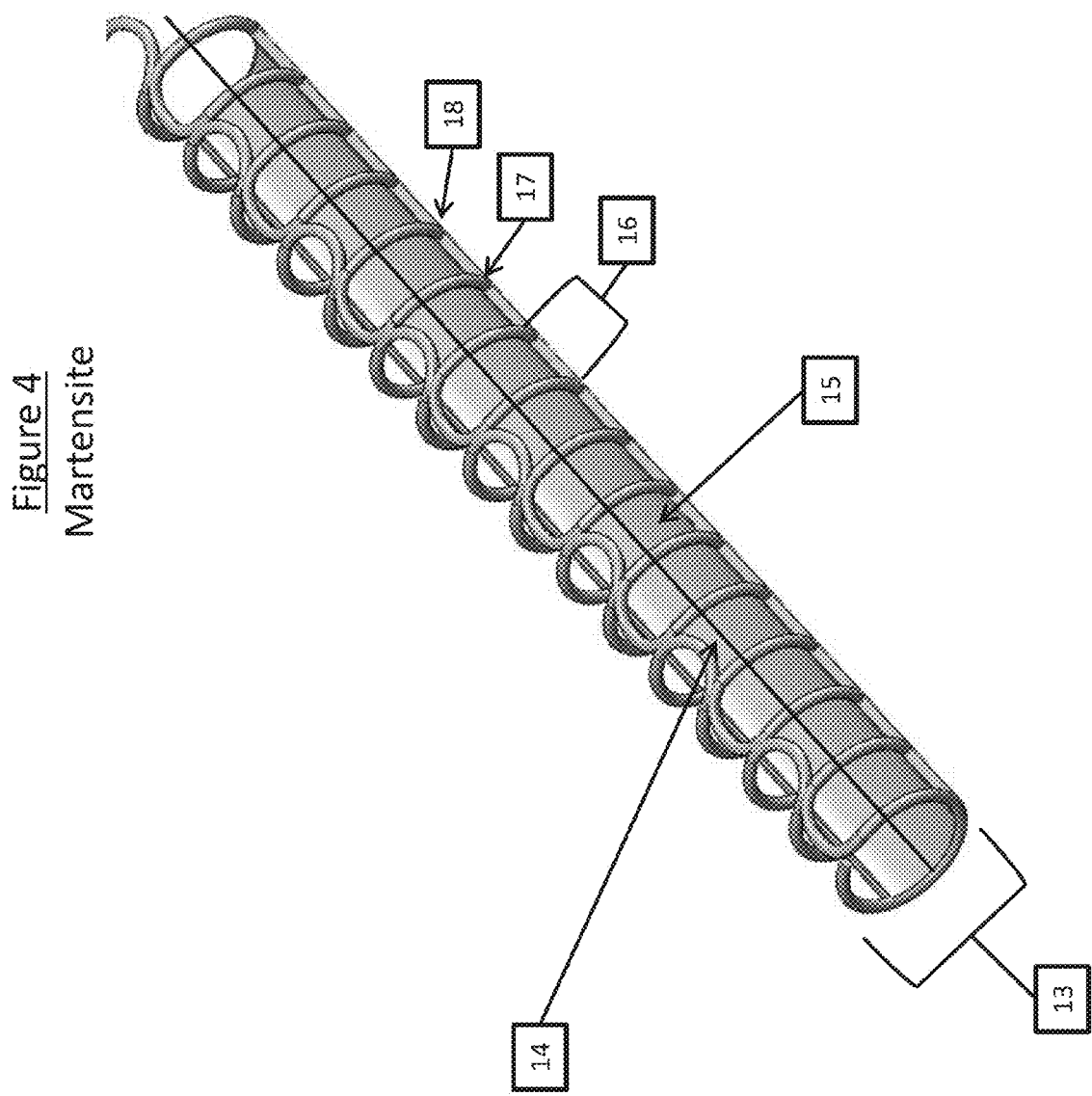
FIG. 4 is an example of a penile prosthesis comprised of a single portion of a shape memory alloy, has ribs in the shape of loops, and wherein the shape memory alloy is in a martensitic phase.

Referring to FIGS. 3 and 4, in a preferred embodiment the ribs 16 may have the profile of a loop. The defining characteristics of this loop are that it has a first-end 17 and a second-end 18, and that both the first-end and second-end are continuous with the backbone 15. The may have any arcuate shape that defines a cylindrical contour of the prosthesis.

Figure 5:
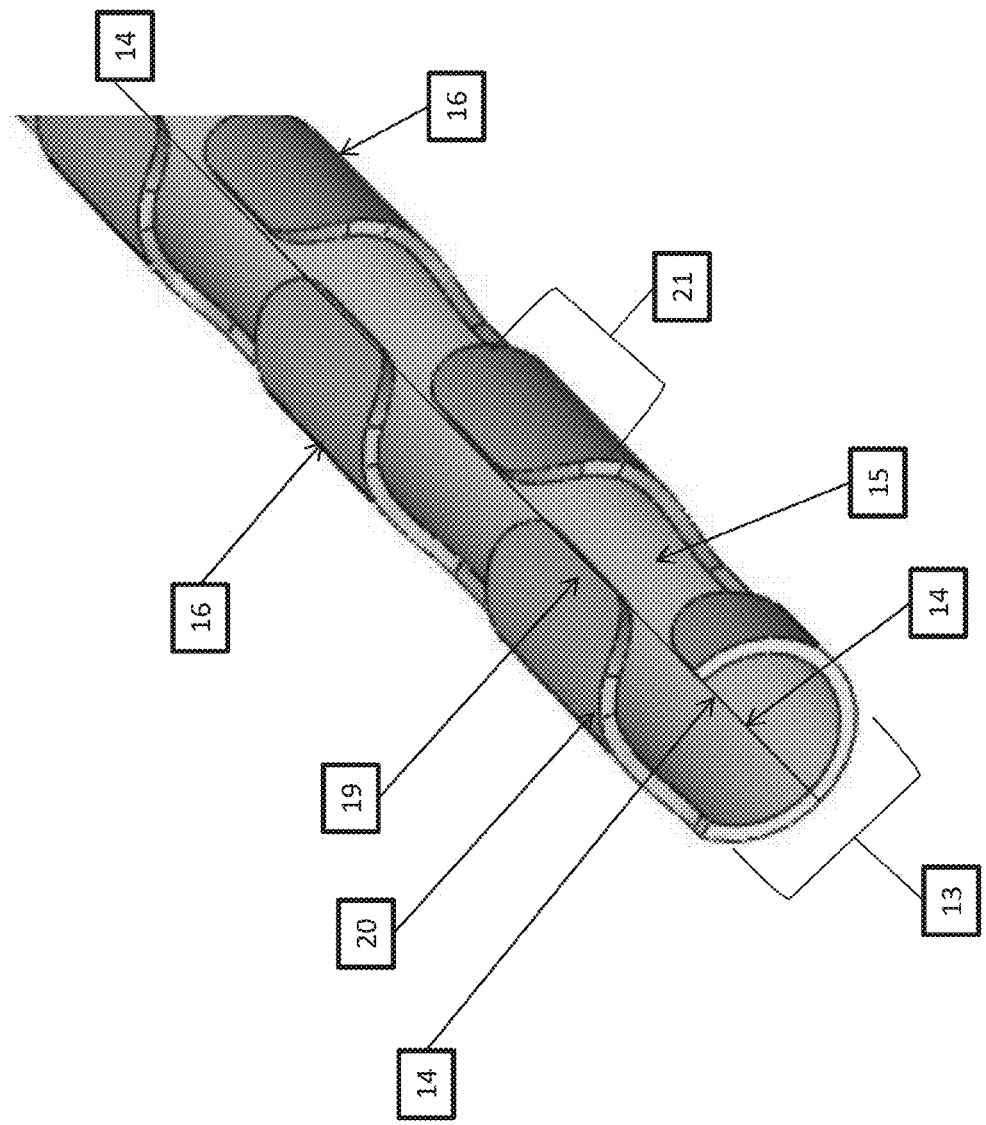
FIG. 5 is an example of a penile prosthesis comprised of a single portion of a shape memory alloy, has ribs, and wherein the shape memory alloy is in an austenite phase.
Figure 6:
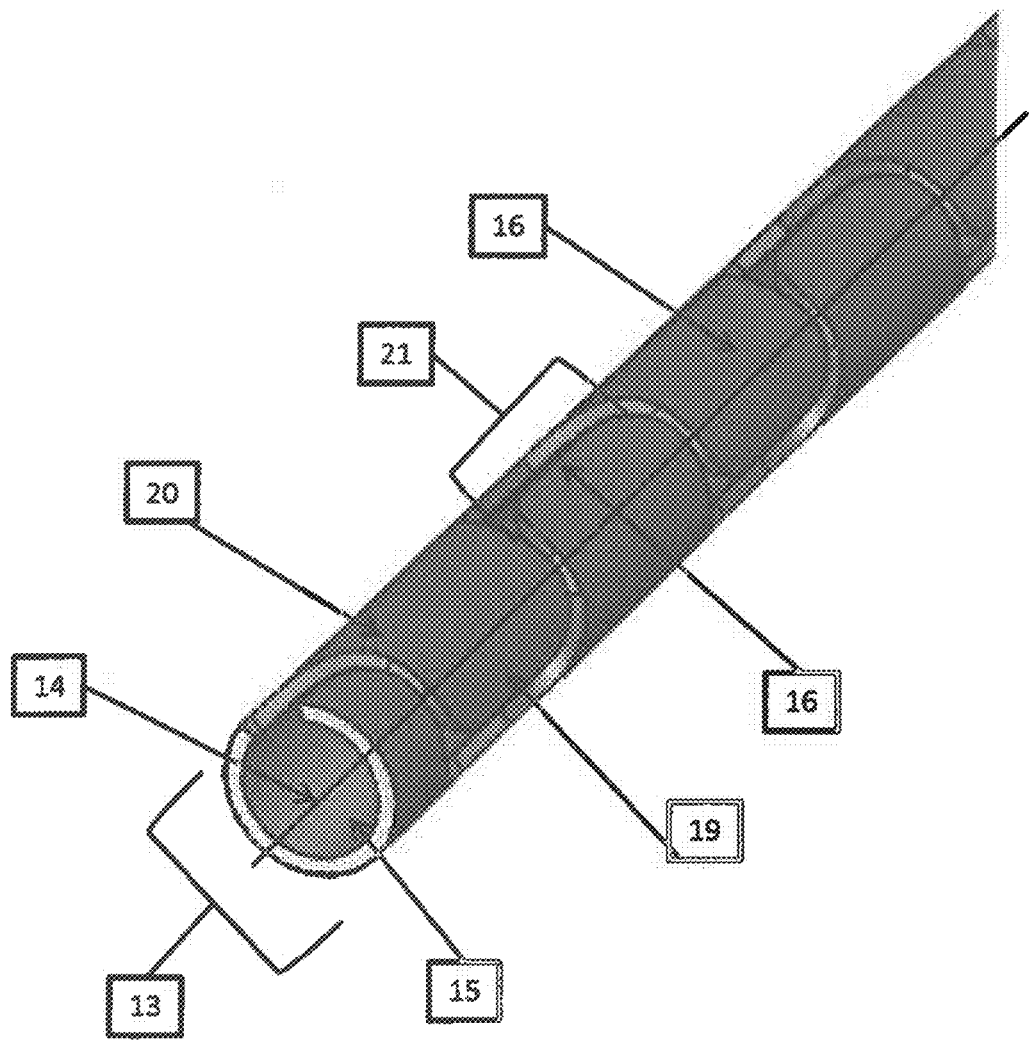
FIG. 6 is an example of a penile prosthesis comprised of a single portion of a shape memory alloy, has ribs, wherein the shape memory alloy is in a martensitic phase.

Referring to FIGS. 5 and 6, in an alternative embodiment the ribs 16 may have the profile of a rib. The defining characteristics of a rib are that it has a first-end 19, a second-end 20, a width 21 greater than or equal to the distance between the first-end and second-end, and that only the first-end is in continuous communication with the backbone 15. The ribs may have any arcuate shape that defines a cylindrical contour of the prosthesis.

Figure 7:
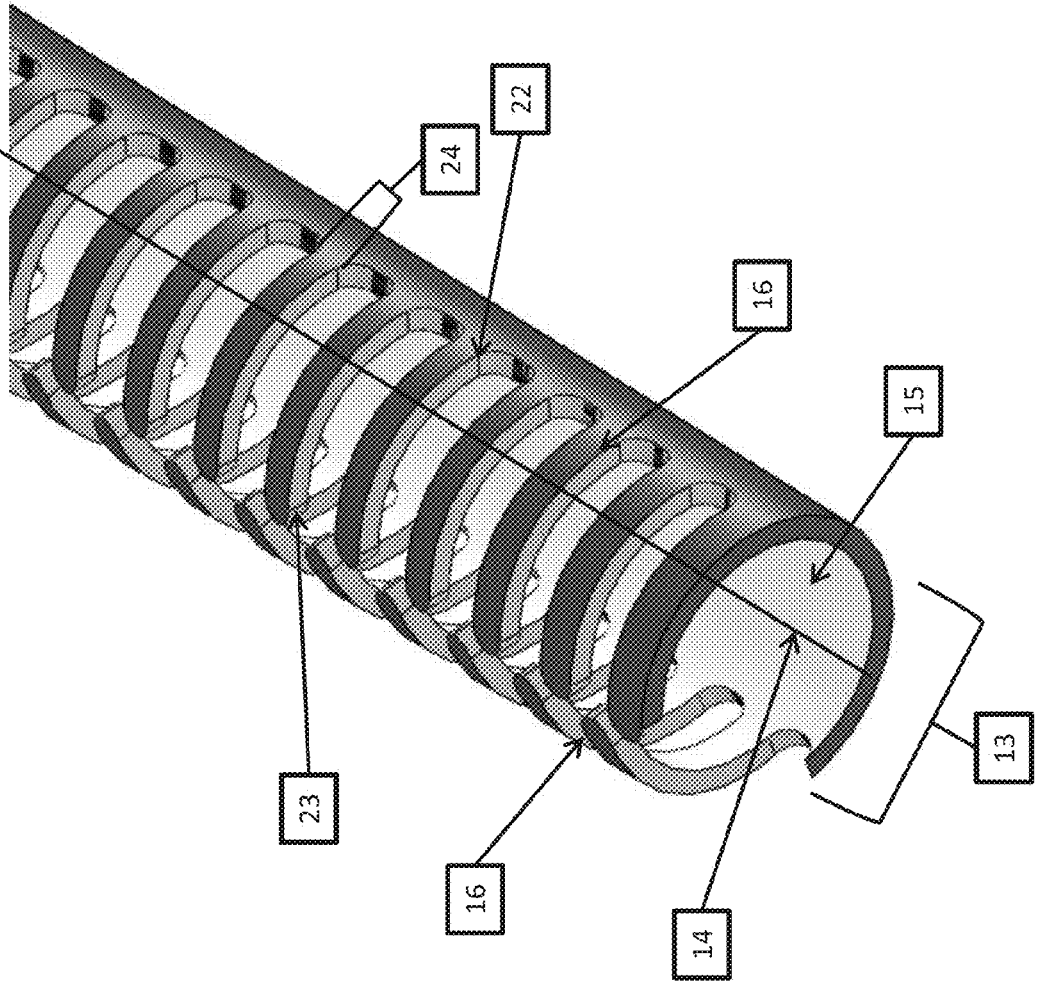
FIG. 7 is an example of a penile prosthesis comprised of a single portion of a shape memory alloy, has ribs, and wherein the shape memory alloy is in an austenite phase.
Figure 8:
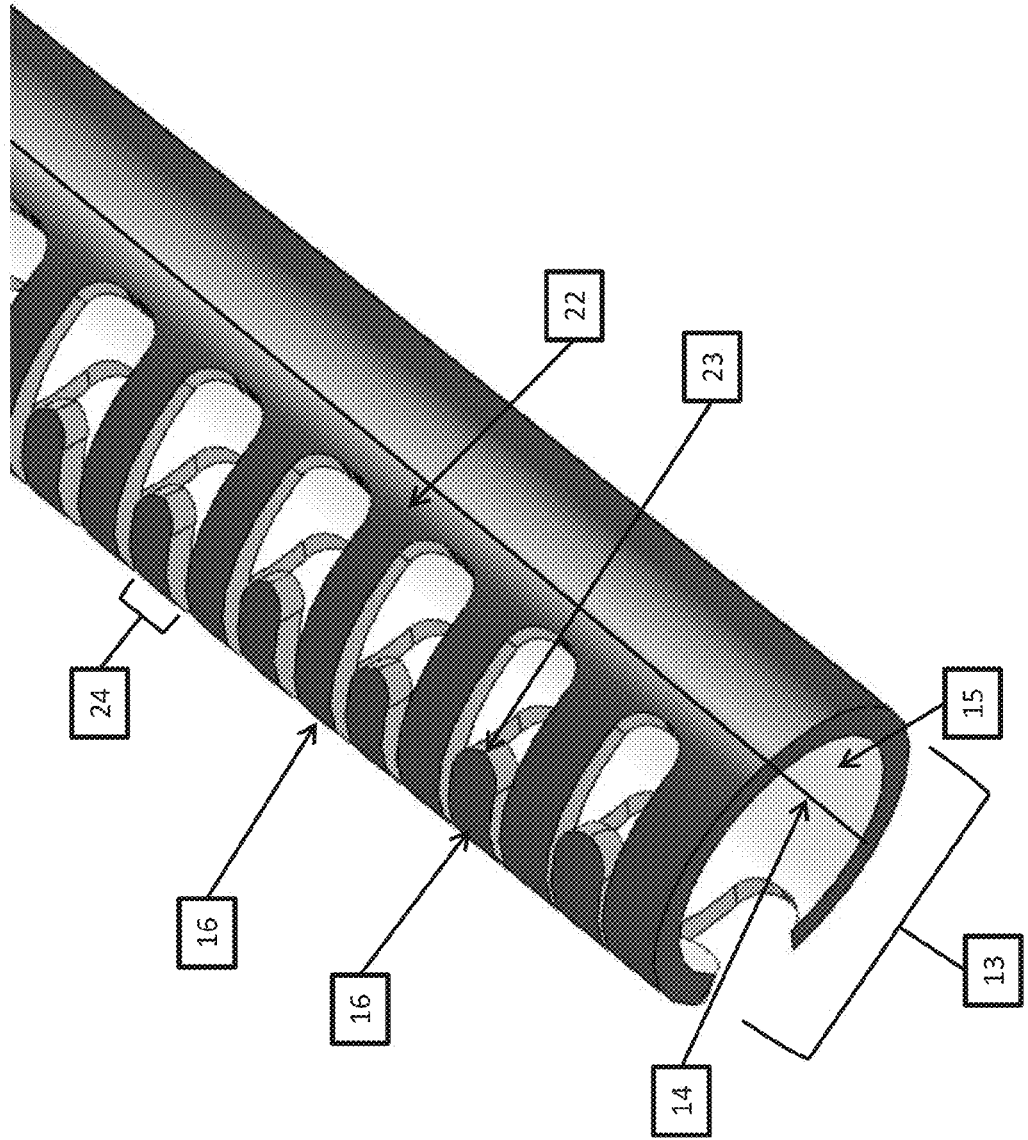
FIG. 8 is an example of a penile prosthesis comprised of a single portion of a shape memory alloy, has ribs, and wherein the shape memory alloy is in a martensitic phase.

Referring to FIGS. 7 and 8, in an alternative embodiment the ribs 16 may have the profile of a whisker. The defining characteristics of a whisker are that is has a first-end 22, a second-end 23, a width 24 less than the distance between the first-end and second-end, and that only the first-end is in continuous communication with the backbone 15. The ribs may have an arcuate shape that defines a cylindrical contour of the prosthesis.

Since the prostheses depicted in FIGS. 3 through 8 and FIG. 15 may be comprised of a shape memory alloy, they may exhibit the hysteresis depicted in FIG. 1. FIGS. 3, 5, and 7 depict the penile prostheses in the austenite state at or above $A_F$ 1. In this state, the prostheses are substantially, if not completely, in their pre-set non-mechanically deformed shape. A defining characteristic of this shape is that it has a substantially, if not completely, cylindrical outer contour. While not necessary, an additional characteristic of the prostheses in the austenite state is that the ribs 16 do not interleave with one another. FIGS. 4, 6, and 8 depict the penile prostheses in a martensitic state at or below $M_F$ 3. In this state, the prostheses are substantially, if not completely, in their mechanically deformed shape and the ribs may interleave with one another.

Referring to FIGS. 1, 3, 5, and 7, in one mode of operation the prosthesis begins in an austenite state at or above $A_F$ 1. It is then exposed to a transition temperature $M_S$ 2, below $A_F$, at which point the amount of alloy in the martensitic phase begins increasing and the amount of the alloy in the austenite phase begins decreasing. Referring the FIGS. 1, 4, 6 and 8, the prosthesis is then further exposed to decreasing temperatures until it reaches $M_F$ 3, at which point the alloy is substantially, if not completely, comprised of a martensitic phase. In this state the prosthesis may be mechanically deformed and the ribs 16 may interleave with one another. Referring to FIGS. 1, 3, 5, and 7, the prosthesis may then be exposed to another transition temperature $A_S$ 4, above $M_F$, at which point the amount of alloy in the martensitic phase begins decreasing, the amount of the alloy in the austenite phase begins increasing, and the prosthesis begins to widen radially while maintaining a substantially cylindrical outer contour. As the temperature continues increasing, the amount of the alloy in the austenite phase continues increasing, and the prosthesis continues to widen radially while maintaining a substantially cylindrical outer contour until reaching $A_F$. At this point, the alloy is substantially, if not completely, comprised of austenite; the prosthesis stops widening radially; and the prosthesis is in its pre-set non-mechanically deformed shape.

Figure 9:
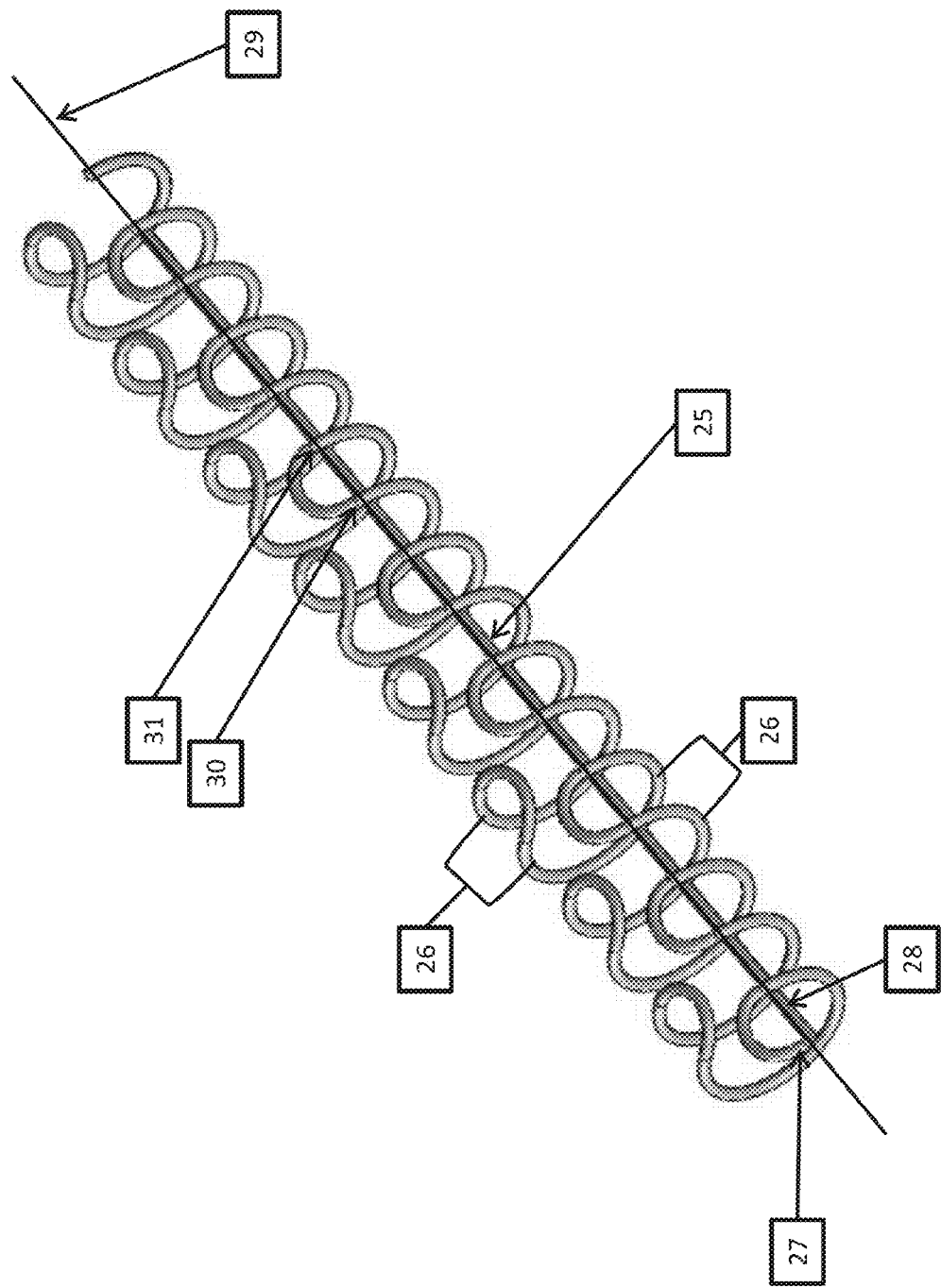
FIG. 9 is an example of a penile prosthesis comprising a backbone made of a shape memory alloy, ribs in the shape of loops comprised of a shape memory alloy wherein the loops must be attached to the backbone, and wherein the shape memory alloys are in an austenite phase.
Figure 10:
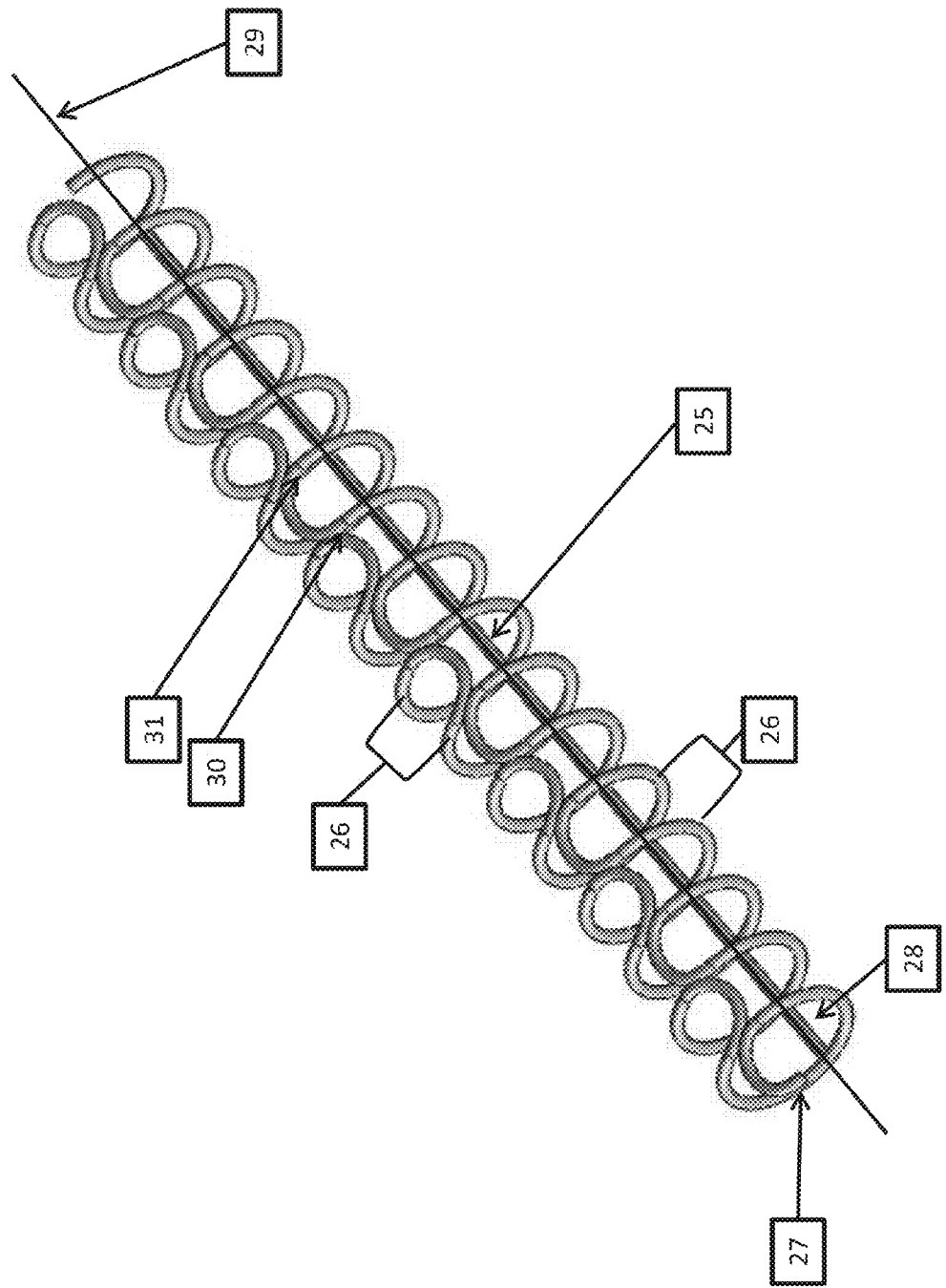
FIG. 10 is an example of a penile prosthesis comprising a backbone made of a shape memory alloy, ribs in the shape of loops comprised of a shape memory alloy wherein the loops must be attached to the backbone, and wherein the shape memory alloys are in a martensitic phase.
Figure 11:
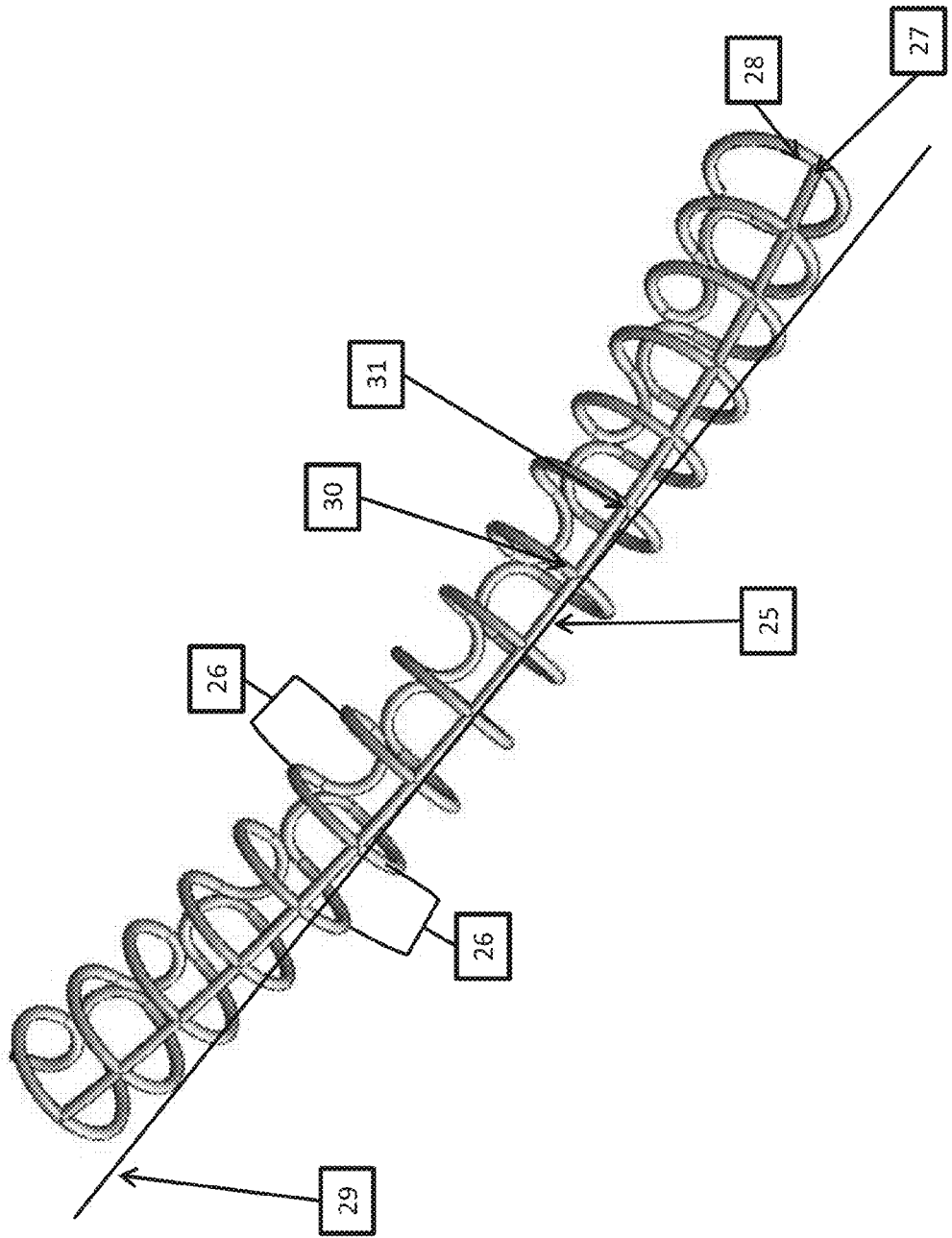
FIG. 11 is an example of a penile prosthesis comprising a backbone made of a shape memory alloy, ribs in the shape of loops comprised of a shape memory alloy wherein the loops must be attached to the backbone, the prosthesis is in a martensitic phase, and the backbone is maintaining a non-linear shape with respect to a longitudinal axis of the device while in the martensitic phase.

Referring to FIGS. 9 through 11, an additional penile prosthesis disclosed herein may be comprised of a backbone 25 and a plurality of ribs 26. In a preferred embodiment the backbone may be comprised of a first shape memory alloy. The backbone may further be comprised of a left-side 27 and a right-side 28, and define a longitudinal axis 29 running through the device. The plurality of ribs may be attached to both the left side and the right side of the backbone and may be attached to the backbone by soldering or by welding.

Still referring to FIGS. 9 through 11, in a preferred embodiment the ribs 26 may be comprised of a shape memory alloy. In a preferred embodiment, the shape memory alloy comprising the ribs is the same as the shape memory alloy comprising the backbone 25. In an alternative embodiment, the shape memory alloy comprising the ribs is different than the shape memory alloy comprising the backbone. In an alternative embodiment, the ribs may be comprised of a two-way shape memory alloy.

Still referring to FIGS. 9 through 11, in a preferred embodiment the ribs 26 may have the profile of a loop. The defining characteristics of a loop are that it has a first-end 30 and a second-end 31, and that both the first-end and second-end are attached to the backbone 25. The loops may have an arcuate shape that defines a cylindrical contour of the prosthesis.

Referring to FIG. 15, in a preferred embodiment of the penile prosthesis, the memory alloy backbone 38 may have various holes 37 of various sizes in various shapes which provide more flexibility to the overall structure of the device. Holes 37 could comprise various shapes including; squares, circles, ovals, rectangles, and diamonds The ribs 39 may have the profile of a rib with a circular closer at each longitudinal end of the device 40. The defining characteristics of a rib are that it has a first-end 39, a second-end 39, a width 39 greater than or equal to the distance 41 between the first-end and second-end, and that only the first-end is in continuous communication with the backbone 38. The ribs may have any arcuate shape that defines a cylindrical contour of the prosthesis.

Since the prosthesis depicted in FIGS. 9 through 11 may be comprised of a shape memory alloy, it may exhibit the hysteresis depicted in FIG. 1. FIG. 9 depicts the penile prostheses in the austenite state at or above $A_F$ 1. In this state, the prosthesis is substantially, if not completely, in its pre-set non-mechanically deformed shape. A defining characteristic of this shape is that the outer contour is substantially, if not completely, cylindrical. While not necessary, an additional characteristic of the prostheses in the austenite state is that the ribs 16 do not overlap. Additionally, the backbone 25 in this state is substantially linear with respect to the longitudinal axis and is able to withstand a compressive load of about 1.50 kilograms or less, Daniel Udelson, "*Biomechanics of male erectile function,*" 4 J. R. Soc. Interface 1039, 1031-1048, (2007). FIGS. 10 and 11 depict the penile prosthesis in a martensitic state at or below $M_F$ 3. In this state, the prosthesis is substantially, if not completely, in its mechanically deformed shape. While not necessary, an additional characteristic of the prostheses in the martensitic state is that the ribs 16 interleave with one another. As depicted in FIG. 11, an additional characteristic of the prosthesis in the martensitic state is that the backbone may be capable of maintaining a nonlinear shape with respect to the longitudinal axis 29.

Referring to FIGS. 1 and 9, in one mode of operation the prosthesis begins in an austenite state at or above $A_F$ 1. Then it is exposed to a transition temperature $M_S$ 2, less then $A_F$, at which point the amount of alloy in the martensitic phase begins increasing and the amount of the alloy in the austenite phase begins decreasing. Referring to FIGS. 1, and 10 through 11, the prosthesis is then further exposed to decreasing temperatures until it reaches $M_F$ 3, at which point the alloy is substantially, if not completely, comprised of a martensitic phase. In this state the prosthesis may be mechanically deformed and the ribs 16 may interleave with one another. As depicted in FIG. 11, the backbone may have a non-linear shape with respect to the longitudinal axis 29 in this state. Referring to FIGS. 1 and 9, the prosthesis may then be exposed to another transition temperature $A_S$ 4, above $M_F$, at which point the amount of alloy in the martensitic phase begins decreasing, the amount of the alloy in the austenite phase begins increasing, and the prosthesis begins to widen radially while maintaining a substantially cylindrical shape outer contour. As the temperature continues increasing, the amount of the alloy in the austenite phase continues increasing, and the prosthesis continues to widen radially while maintaining a substantially cylindrical contour until reaching $A_F$. At this point, the alloy is substantially, if not completely, comprised of austenite; the prosthesis stops widening radially; and the prosthesis is in its pre-set non-mechanically deformed shape.

The pre-set non-mechanically deformed shape of the ribs does not necessarily need to lead to a radial widening of the prosthesis. The pre-set shape of the ribs may also lead to a radial contraction of prosthesis, or a portion of the prosthesis. In an alternative embodiment (NOT SHOWN), the ribs may have a first section and a second section. The first section may widen radially while maintaining a substantially cylindrical outer contour and the second section may contract radially while maintaining a substantially cylindrical contour. Alternatively, the ribs may comprise a third section, the third section also contracting. The third section contracts to a greater degree than the second section and maintains a substantially cylindrical outer contour.

Figure 12:
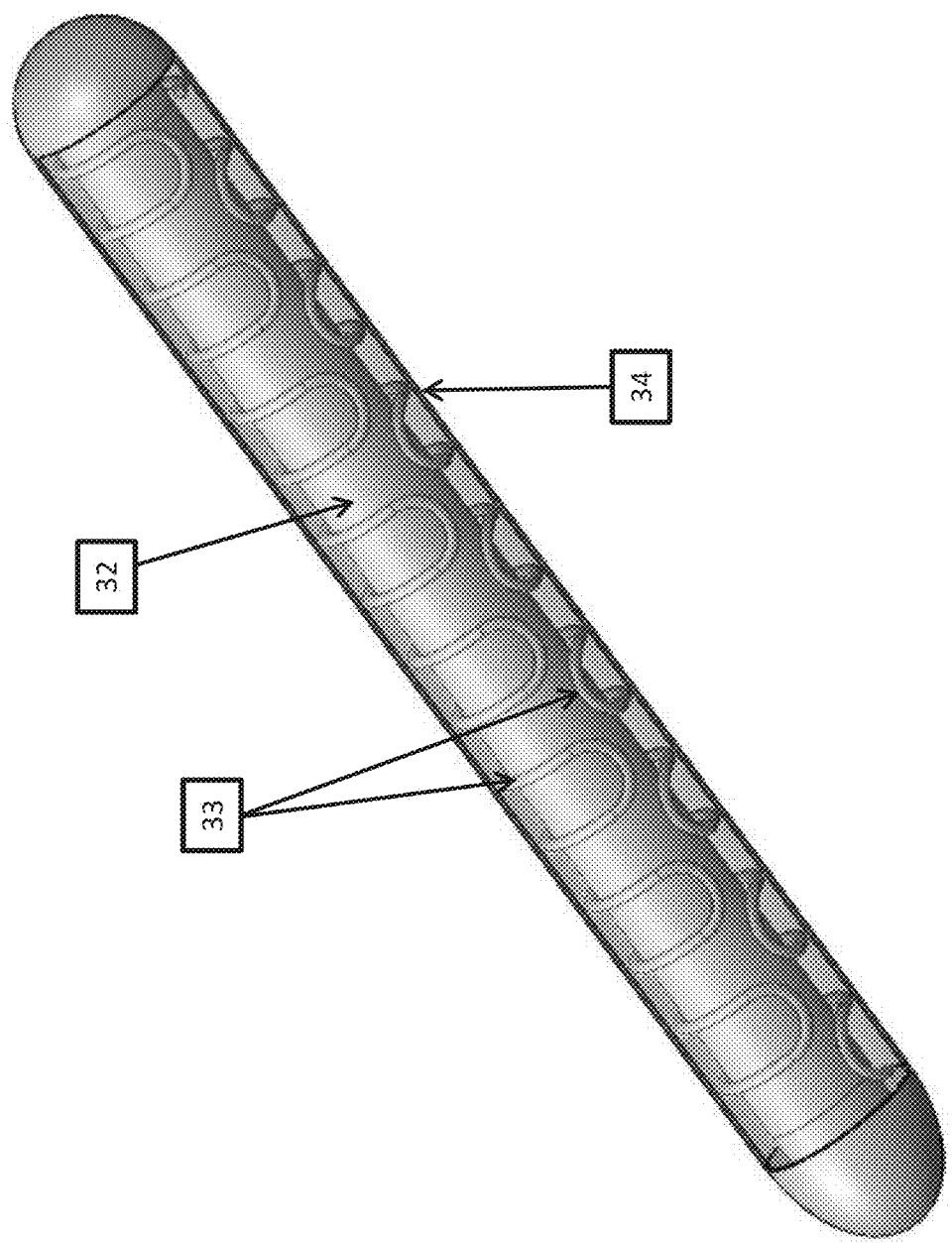
FIG. 12 is a depiction of an additional prosthesis comprising a core, an exoskeleton comprised of a shape memory alloy surrounding the core, and a heat-conducting sheath surrounding the exoskeleton and core.
Figure 13:
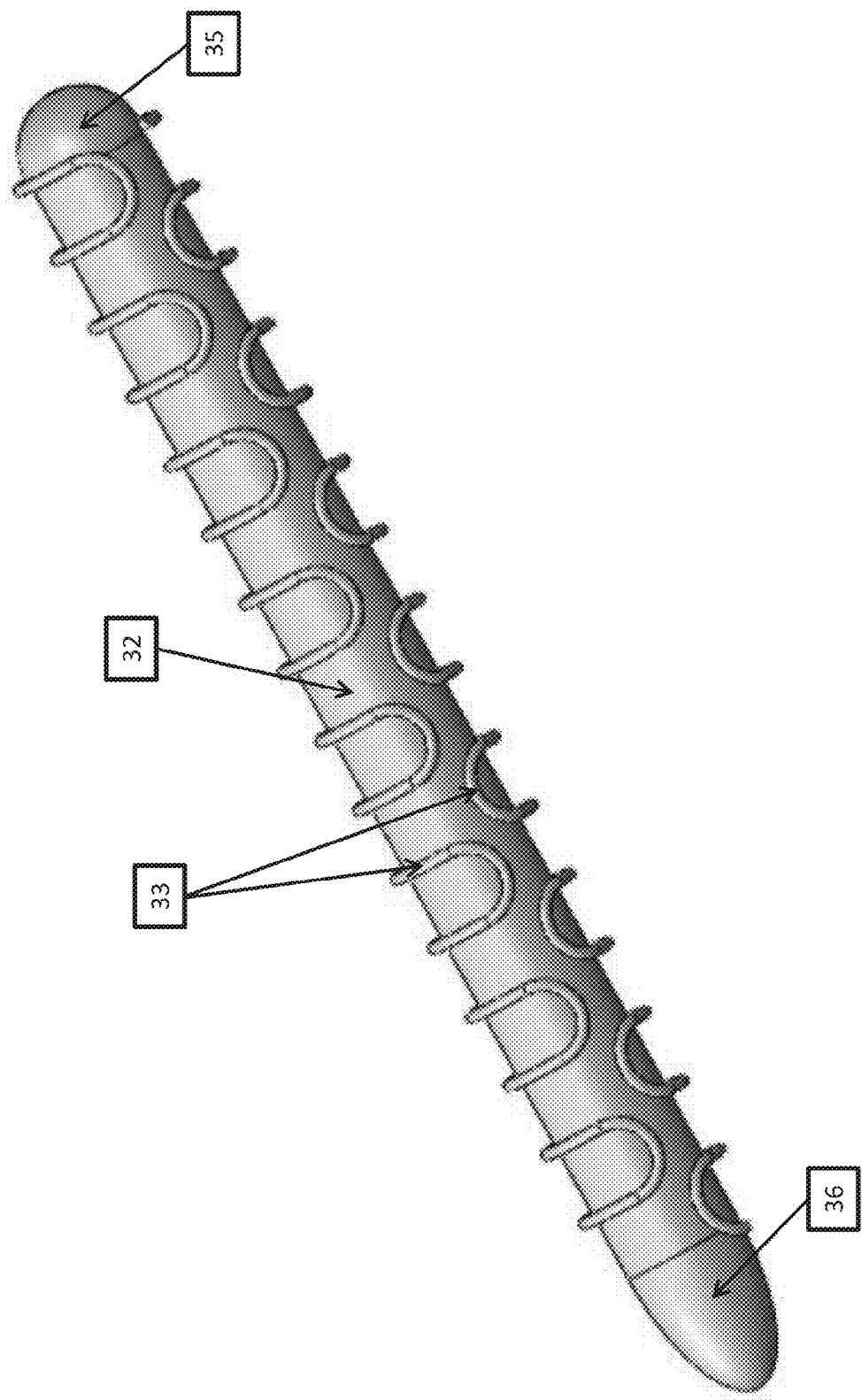
FIG. 13 is a depiction of the core having different shaped ends.

Referring to FIGS. 12 and 13, prosthesis implantable in the corpus cavernosa disclosed herein may further comprise a core 32 surrounded by an exoskeleton 33 comprised of a shape memory alloy. The core and exoskeleton may be further surrounded by a sheath 34 of heat-conducting stretchable material. In a preferred embodiment the core is comprised of saline. In a more preferred embodiment, the core may be comprised of a heat-retaining gel. In an even more preferred embodiment, the core may be comprised of a biocompatible heat-retaining gel. In a preferred embodiment, the exoskeleton is comprised of a nickel-titanium shape memory alloy disclosed herein.

Referring to FIG. 13, the core 32 may comprise a first-end 35 and a second-end 36. In a preferred embodiment, the first-end may have an outward-facing convex shape. In a preferred embodiment, the second-end may have an outward-facing substantially conical shape.

Figure 14:
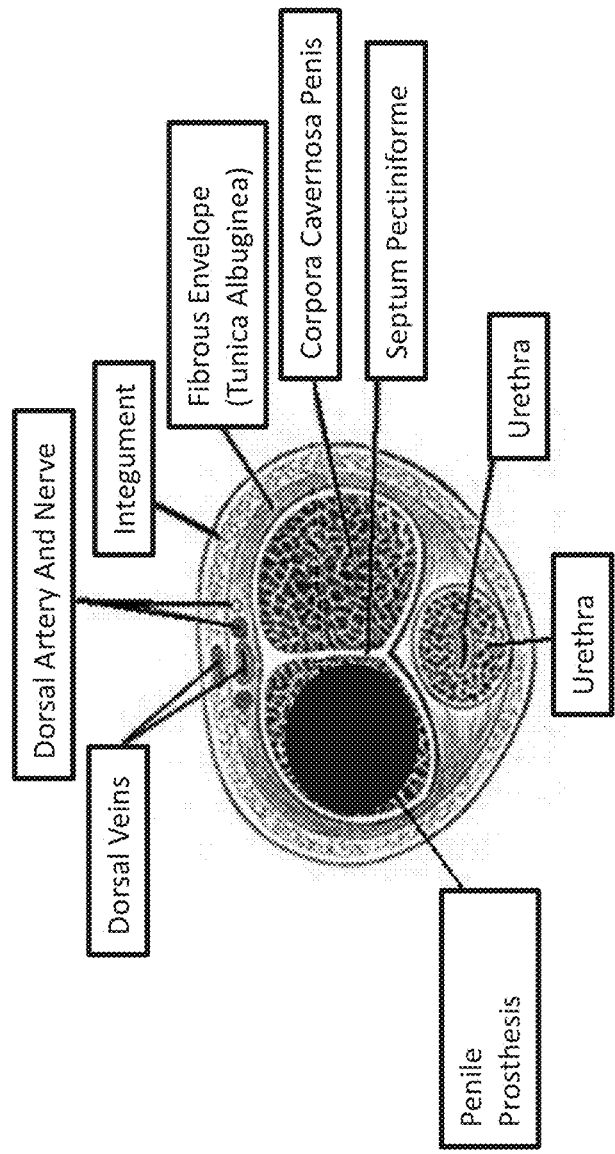
FIG. 14 is a cross-section of the penis depicting the implantation location the penile prostheses disclosed herein.

Referring to FIG. 14, a prosthesis disclosed herein may be implanted in a penile corpus cavenosa. In use, at least one prosthesis as disclosed herein is implanted in each penile corpus cavernosa through a skin incision after dilatation of the corporal bodies is achieved.

In use, the entire prosthetic apparatus comprises of 2 erective bodies that are inserted in the compora cavernosa of the penis. In the austenitic state each erective body is able to withstand at least 1.50 kilograms in the axial direction without buckling. Such a force level has been shown in the literature to be sufficient to the natural erective body (the penis) for coitus, Daniel Udelson, "*Biomechanics of male erectile function*," 4 J. R. Soc. Interface 1039, 1031-1048, (2007). The design of the prosthesis is such that one erective body (out of two) could be sufficient for coitus. The prosthesis claimed herein was tested using an Instron machine. An Instron machine is able to measure the displacement and the force generated on a sample for a specific period of time. The prosthesis claimed exhibited properties capable of withstanding a force of at least 1.5 kilograms in the axial direction without buckling.

In use, beginning from a flaccid state, a heat source such as a warm pack having a temperature greater than or equal to about the $A_F$ of the shape memory alloy is placed over the penis. Over time there is heat transfer to the implanted prosthesis and the temperature of the shape memory alloy rises above penile resting temperature, continues to increase above the $A_S$ of shape memory alloy, and continues increasing until the shape memory alloy reaches $A_F$. In this configuration an implanted prosthesis is in its erect conformation and intercourse may ensue. The structural mechanical design of the prosthesis and its super elastic properties are such that the erective body is able to maintain its structural shape during normal force of coitus by elastically buttressing the corpora cavernosa. After coitus, the penis is then actively cooled with an ice pack or shower. Over time there is heat removal from the implanted prosthesis and the temperature of the shape memory alloy decreases below penile resting temperature, continues to decrease below $M_S$ of the shape memory alloy, and continues to decrease until the shape memory alloy reaches $M_F$. In this configuration the penis is in a flaccid state, and may be discretely tucked away.

It should be understood that the methods, procedures, operations, devices, and systems illustrated in FIGS. 1 through 14 may be modified without departing from the spirit of the invention. For example, these methods, procedures, operations, devices, and systems may comprise more or fewer steps or components than appear herein, and these steps or components may be combined with one another, in part or in whole.

Furthermore, the present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein will be apparent to those skilled in the art from the foregoing descriptions.

It is to be understood that this disclosure is not limited to particular methods, reagents, compounds compositions or biological systems, which can, of course, vary. It is also to be understood that the terminology used herein is for the purpose of describing particular embodiments only, and is not intended to be limiting. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are intended as "open" terms (e.g., the term "including" should be interpreted as "including but not limited to," the term "having" should be interpreted as "having at least," the term "includes" should be interpreted as "includes but is not limited to," etc.).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

As will also be understood by one skilled in the art, all language such as "up to," "at least," "greater than," "less than," and the like include the number recited and refer to ranges which can be subsequently broken down into subranges as discussed above.

Finally, as will be understood by one skilled in the art, a range includes each individual member. Thus, for example, a group having 1-3 members refers to groups having 1, 2, or 3 members. Similarly, a group having 1-5 members refers to groups having 1,2,3,4, or 5 members, and so forth.

What is claimed is:

1. A penile prosthesis implantable in a corpus cavernosum for facilitating an erection, the penile prosthesis comprises:
   a) an exoskeleton comprising a shape memory alloy having a dimension that enlarges radially in response to an increase in temperature around said prosthesis and a cylindrical outer contour along a longitudinal axis;
   b) a heat-conducting sheath surrounding the exoskeleton; and
   c) a core located within the exoskeleton, the core retaining a fluid within the exoskeleton,
   wherein the exoskeleton, the heat-conducting sheath and the core are configured to remain in the corpus cavernosum before, during and after the erection.

2. The penile prosthesis of claim 1, wherein the longitudinal axis of the cylindrical outer contour comprises:
   a) a backbone comprising the shape memory alloy; and
   b) at least two ribs comprising the shape memory alloy.

3. The penile prosthesis of claim 2, wherein the ribs widen radially while maintaining substantially cylindrical contour at or above a transition temperature.

4. The penile prosthesis of claim 2, wherein the backbone reverts to a linear shape defined by said longitudinal axis at or above a transition temperature.

5. The penile prosthesis of claim 2, wherein the backbone maintains a non-linear shape with respect to said longitudinal axis at a temperature below a transition temperature.

6. The penile prosthesis of claim 2, wherein the backbone comprises a width equal to or less than one half a circumference of said cylindrical outer contour.

7. The penile prosthesis of claim 2, wherein the backbone comprises holes, wherein a surface area of said holes does not exceed a surface area of said shape memory alloy of said backbone.

8. The penile prosthesis of claim 2, wherein the backbone comprises a left side and a right side.

9. The penile prosthesis of claim 8, wherein the ribs are attached to both the right side and left side of said backbone having a substantially arcuate shape defining the cylindrical outer contour of the penile prosthesis.

10. The penile prosthesis of claim 1, wherein the shape memory alloy comprises a thickness less than about two millimeters.

11. The penile prosthesis of claim 1, wherein the fluid is selected from a saline solution or a heat-retaining gel.

12. The penile prosthesis of claim 11, wherein the fluid comprises a heat-retaining gel.

13. The penile prosthesis of claim 12, wherein the heat-retaining gel comprises a biocompatible composition.

14. A method of simulating an erection of a penis comprising heating a penile prosthesis implanted in the corpus cavernosum to a temperature at which a dimension of the penile prosthesis enlarges radially,
   wherein the penile prosthesis comprises:
   a) an exoskeleton comprising a shape memory alloy having a dimension that enlarges radially in response to an increase in temperature around said prosthesis and a cylindrical outer contour along a longitudinal axis;
   b) a heat-conducting sheath surrounding the exoskeleton; and
   c) a core located within the exoskeleton, the core retaining the fluid within the exoskeleton,
   wherein the exoskeleton, the heat-conducting sheath and the core are configured to remain in the corpus cavernosum before, during and after the erection.

15. The method of claim 14, wherein the shape memory alloy comprises a thickness less than about two millimeters.

16. The method of claim 14, wherein the cylindrical outer contour along the longitudinal axis comprises:
   a) backbone, and
   b) at least two ribs attached to the backbone,
   wherein the cylindrical outer contour along the longitudinal axis can withstand at least 1.5 kilograms of force without buckling.

17. The method of claim 14, wherein the fluid is selected from a saline solution or a heat-retaining gel.

18. The method of claim 17, wherein the fluid comprises a heat-retaining gel.

19. The method of claim 18, wherein the heat-retaining gel comprises a biocompatible composition.

20. A method of creating an erection of a penis implanted with a penile prosthesis in a corpus cavernosum, comprising heating the penile prosthesis to a temperature at which the prosthesis enlarges radially,
   wherein the penile prosthesis comprises:
   a) an exoskeleton comprising a shape memory alloy having a dimension that enlarges radially in response to an increase in temperature around said prosthesis and a cylindrical outer contour along a longitudinal axis;
   b) a heat-conducting sheath surrounding the exoskeleton; and
   c) a core located within the exoskeleton, the core retaining the fluid within the exoskeleton,
   wherein the exoskeleton, the heat-conducting sheath and the core are configured to remain in the corpus cavernosum before, during and after the erection.

21. The method of claim 20, wherein the cylindrical outer contour along a longitudinal axis comprises:
   a) a backbone, and
   b) at least two ribs attached to the backbone,
   wherein the cylindrical outer contour along the longitudinal axis can withstand at least 1.5 kilograms of force without buckling.

22. The method of claim 20, wherein the fluid is selected from a saline solution or a heat-retaining gel.

23. The method of claim 22, wherein the fluid comprises a heat-retaining gel.

24. The method of claim 23, wherein the heat-retaining gel comprises a biocompatible composition.

25. A penile prosthesis implantable in a corpus cavernosum comprising:
   a) a shape memory alloy having a dimension that enlarges radially in response to an increase in temperature around said prosthesis and a cylindrical outer contour along a longitudinal axis;
   b) a heat-conducting sheath surrounding the shape memory alloy; and
   c) a core retaining a fluid comprising a heat-retaining gel,
   wherein the shape memory alloy, the heat-conducting sheath and the core are configured to remain in the penile prosthesis after implantation in the corpus cavernosum.

26. The penile prosthesis of claim 25, wherein the heat-retaining gel comprises a biocompatible composition.

27. The penile prosthesis of claim 25, wherein the longitudinal axis of the cylindrical outer contour comprises:
   i) a backbone comprising the shape memory alloy; and
   ii) at least two ribs comprising the shape memory alloy.

* * * * *